US010788154B2

(12) United States Patent
Dudar et al.

(10) Patent No.: US 10,788,154 B2
(45) Date of Patent: Sep. 29, 2020

(54) INFUSION LINE MANAGEMENT SYSTEM

(71) Applicants: Baxter International Inc., Deerfield, IL (US); Baxter Healthcare S.A., Glattpark (CH)

(72) Inventors: Thomas Edward Dudar, Palatine, IL (US); Steven Clarence Jepson, Vernon Hills, IL (US)

(73) Assignees: BAXTER INTERNATIONAL INC., Deerfield, IL (US); BAXTER HEALTHCARE S.A., Glattpark (Opfikon) (CH)

(*) Notice: Subject to any disclaimer, the term of this patent is extended or adjusted under 35 U.S.C. 154(b) by 0 days.

(21) Appl. No.: 14/079,108

(22) Filed: Nov. 13, 2013

(65) Prior Publication Data
US 2014/0130909 A1 May 15, 2014

Related U.S. Application Data

(60) Provisional application No. 61/725,692, filed on Nov. 13, 2012.

(51) Int. Cl.
F16L 55/00 (2006.01)
B42D 15/00 (2006.01)
(Continued)

(52) U.S. Cl.
CPC ............... F16L 55/00 (2013.01); A61M 5/14 (2013.01); B42D 15/00 (2013.01);
(Continued)

(58) Field of Classification Search
CPC .. G09F 3/0288; G06F 19/326; A61M 5/1413; G06Q 10/08
(Continued)

(56) References Cited

U.S. PATENT DOCUMENTS 4,526,404 A 7/1985 Vazquez
4,943,279 A 7/1990 Samiotes et al.
(Continued)

FOREIGN PATENT DOCUMENTS

CN 101143234 A 3/2008
EP 1748401 A2 1/2007
(Continued)

OTHER PUBLICATIONS

PCT Search Report issued in Int'l. App. No. PCT/US2013/069832, dated Mar. 2, 2014.
(Continued)

Primary Examiner — Robert W Morgan
Assistant Examiner — Edward B Winston, III
(74) Attorney, Agent, or Firm — Greer, Burns & Crain, Ltd.

(57) ABSTRACT

An infusion line management system is provided, including a label generating device receiving prescription information for one or more patient prescriptions, the received information being used to generate, for each of the one or more prescriptions, a label including a master label and one or more sub-labels related to the corresponding prescription; each master label includes at least information related to the prescription and an indicator identifying a particular portion of a patient infusion system to which the prescription should be connected; and the one or more sub-labels each include the indicator, the one or more sub-labels being individually removable from the master label and affixable to locations throughout the patient infusion system.

16 Claims, 4 Drawing Sheets

(51) Int. Cl.
*G06F 19/00* (2018.01)
*G16H 20/17* (2018.01)
*A61M 5/14* (2006.01)

(52) U.S. Cl.
CPC ......... *G06F 19/3468* (2013.01); *G16H 20/17* (2018.01); *Y10T 137/8158* (2015.04)

(58) Field of Classification Search
USPC ........................................................ 705/2–3
See application file for complete search history.

(56) References Cited

U.S. PATENT DOCUMENTS

| | | | |
|---|---|---|---|
| 5,048,870 A | 9/1991 | Mangini et al. | |
| 5,090,779 A | 2/1992 | Kramer | |
| 5,180,287 A | 1/1993 | Natwick et al. | |
| 5,329,927 A | 7/1994 | Gardineer et al. | |
| 5,766,716 A | 6/1998 | Barry | |
| 5,782,495 A | 7/1998 | Grosskopf et al. | |
| 5,799,981 A | 9/1998 | Tung et al. | |
| 5,855,395 A | 1/1999 | Foote et al. | |
| 5,958,536 A | 9/1999 | Gelsinger et al. | |
| 5,974,708 A | 11/1999 | Webb et al. | |
| 6,035,568 A | 3/2000 | Grosskopf et al. | |
| 6,142,008 A | 11/2000 | Cole et al. | |
| 6,410,111 B1* | 6/2002 | Roth ..................... | G09F 3/0288 283/81 |
| 6,468,242 B1 | 10/2002 | Wilson et al. | |
| 6,685,227 B2 | 2/2004 | Merry et al. | |
| 7,092,797 B2 | 8/2006 | Gaines et al. | |
| 7,455,662 B2 | 11/2008 | Kraushaar | |
| 7,933,780 B2 | 4/2011 | De La Huerga | |
| 8,266,878 B2* | 9/2012 | Luciano, Jr. .......... | A61J 7/0069 53/473 |
| 8,317,770 B2 | 11/2012 | Miesel et al. | |
| 8,571,881 B2* | 10/2013 | Rousso .................. | A61B 5/417 705/2 |
| 8,597,271 B2 | 12/2013 | Langan et al. | |
| 8,808,249 B2 | 8/2014 | Langan et al. | |
| 8,962,707 B2 | 2/2015 | Singh | |
| 2002/0013551 A1* | 1/2002 | Zaitsu .................. | A61M 5/1413 604/151 |
| 2002/0038392 A1 | 3/2002 | De La Huerga | |
| 2002/0056989 A1 | 5/2002 | Lewis-Leander | |
| 2002/0077582 A1 | 6/2002 | Mehdi et al. | |
| 2003/0135388 A1 | 7/2003 | Martucci et al. | |
| 2003/0140928 A1 | 7/2003 | Bui et al. | |
| 2006/0047538 A1* | 3/2006 | Condurso ............. | G06F 19/326 705/3 |
| 2006/0081255 A1 | 4/2006 | Miller et al. | |
| 2006/0206356 A1 | 9/2006 | Vanderveen | |
| 2006/0265246 A1 | 11/2006 | Hoag | |
| 2007/0088286 A1 | 4/2007 | Brier | |
| 2007/0107517 A1 | 5/2007 | Arnold | |
| 2007/0208595 A1* | 9/2007 | Ohmura .............. | G06F 19/3462 705/2 |
| 2007/0233520 A1 | 10/2007 | Wehba et al. | |
| 2008/0046288 A1* | 2/2008 | Menon .................. | G06Q 10/06 705/3 |
| 2008/0131362 A1* | 6/2008 | Rousso .................. | A61B 5/417 424/1.11 |
| 2009/0053071 A1 | 2/2009 | Wang et al. | |
| 2009/0150484 A1 | 6/2009 | Roberts | |
| 2009/0177769 A1 | 7/2009 | Roberts | |
| 2009/0242631 A1* | 10/2009 | Wishnatzki ........... | G06Q 10/08 235/385 |
| 2010/0094653 A1* | 4/2010 | Tribble ................. | G06F 19/326 705/3 |
| 2011/0071844 A1 | 3/2011 | Cannon et al. | |
| 2013/0289496 A1 | 10/2013 | Langan et al. | |
| 2014/0067425 A1 | 3/2014 | Dudar et al. | |
| 2014/0262252 A1 | 9/2014 | Slepicka et al. | |
| 2014/0326629 A1 | 11/2014 | Langan et al. | |

FOREIGN PATENT DOCUMENTS

| | | |
|---|---|---|
| JP | 2005-284855 A | 10/2005 |
| JP | 2006-296912 A | 11/2006 |
| JP | 2010-264255 A | 11/2010 |
| WO | 2003098534 A1 | 11/2003 |
| WO | 2014/055434 | 4/2014 |

OTHER PUBLICATIONS

Statement in accordance with the Notice from the EP Patent Office dated Oct. 1, 2007, concerning business methods; Nov. 1, 2007.
International Search Report for International Application No. PCT/US2013/058532, dated Jan. 9, 2014.
New Zealand Examination Report for corresponding NZ Application No. 709436, dated Nov. 1, 2016.
Vanhoenacker, Mark, "The Beauty of the Airline Baggage Tag", Slate.com, Archive date Oct. 4, 2012. <https://web.archive.org/web/20121004173729/http://www.slate.com/articles/life/design/2012/10airline_baggage_tags_how_their_brilliant_design_gets_bags_from_point_a_to_point_b__single.html> Accessed Oct. 26, 2016.
"The Hospicode® Colour Coded Medilabel System", www.henleysmed.com, Archive date Aug. 24, 2012. <https://web.archive.org/web/20120824144707/http://www.henleysmed.com/page/hospicode-colour-coded-medilabel-system> Accessed Oct. 26, 2016.
Lipstein, Evan, "ColorSafe IV Lines™ colored IV Infusion Lines Combat Medication Errors in Hospitals & Healthcare Facilities—ColorSafe IV Lines™Improve Patient Safety During IV Therapy", www.prweb.com, Archive date Oct. 8, 2009. <https://web.archive.org/web/20091008004223/http://www.prweb.com/releases/colorsafe_IV/medical_products/prweb2929304.htm>.
"Ceftriaxone (Rocephin): Is your doctor following directions?", thetickthatbitme.com, Archive date Jun. 1, 2012. <https://web.archive.org/web/20120601015444/http://thetickthatbitme.com/tag/iv-therapy/> Accessed Oct. 26, 2016.
Chinese Office Action for corresponding CN Application No. 201380059427.2, dated Jan. 26, 2017.
Russian Search Report for corresponding Russian Patent Application No. 2015122409, dated Nov. 10, 2017.
Japanese Office Action for corresponding Japanese Application No. 2015-542028, dated Oct. 31, 2017.
Russian Office Action for corresponding Russian Patent Application No. 2015122409, dated Aug. 21, 2018.
European Search Report for corresponding European Patent Application No. 13796201.5 dated Jun. 27, 2018.
Merry et al., "A New Infusion Syringe Label System Designed to Reduce Task Complexity During Drug Preparation," Anaesthesia (2007), 62(), pp. 486-491.

* cited by examiner

INFUSION LINE MANAGEMENT SYSTEM

RELATED APPLICATION

This application claims 35 U.S.C. § 119(e) priority from U.S. Ser. No. 61/725,692 filed Nov. 13, 2012.

FIELD OF THE INVENTION

This invention relates to a system for identifying and managing patient infusion system configurations, including medication containers, tubing sets, access ports, pump channels, and catheters.

BACKGROUND

Errors in administration of medication through a patient infusion system can result from many causes, including misconnections. Accordingly, to reduce the potential for such errors, professional guidelines and/or standard operating procedures obligate clinicians, such as nurses, to perform "line management," also known as line tracing, numerous times throughout their working shifts. Line management involves verifying that each medication, typically contained in a bag, bottle, or syringe, is routed through tubing to the correct catheter and the tubing is associated with the correct pump channel (if an infusion pump is used). The activity further includes verifying that it is safe to join two or more tubing segments containing different medications and/or flowing at different rates. By way of example, a nurse may perform line management for each patient when starting a shift, when receiving a patient from another facility, another area of the hospital, or another clinician, and just prior to administration of an intravenous medication. Repeated performance of the detailed line management procedure imposes a time burden on the clinicians, and is prone to errors, particularly as the complexity of a patient's overall infusion tubing system increases. That is, multiple tubing sets, medications, junctions, access ports, pump channels, and catheters both increase the amount of time required to perform line management and introduce additional opportunities for error.

While the medication container typically arrives from the pharmacy with a simple label already applied to it, clinicians often manually label infusion setups at various locations throughout the tubing system to facilitate line management. Generally, the labeling is crude, using materials on hand such as medical tape wrapped around the tubing and labeled with identifying information such as the medication name. This labeling is repeated at several points throughout the system. For example, labels may be placed at one or more of the spike end and the catheter connection end of the tubing set, at each access port and junction, on the roller clamp and slide clamp, on the catheter, and on the pump channel itself. If the medication being delivered is changed but the tubing system is reused, the labels must be removed and replaced with new labels bearing the new medication's name.

Accordingly, there is a need to streamline the line management process, both to save clinician time and to reduce the possibility of errors. Additionally, there is a need for a more complete and professional label system that is cost effective.

SUMMARY

An infusion line management system addresses these needs. The system allows for a streamlined clinician workflow that helps the clinician map patient infusions. Further, the labels produced using the system are relatively low cost, professional, uniform, and relatively easy to read.

In a first aspect, an infusion line management system includes a label generating device that receives prescription information for one or more patient prescriptions. The received prescription information is used to generate, for each of the one or more prescriptions, a label including a master label and one or more related sub-labels related to the corresponding prescription. Each generated master label includes at least information related to the prescription and an indicator identifying a particular portion of a patient infusion system to which the prescription should be connected. Similarly, each of the one or more related sub-labels includes the indicator. The sub-labels are individually removable from the master label and affixable to locations throughout the patient infusion system.

In another aspect, a non-transitory computer readable medium is configured for storing instructions that, when executed by a processor, cause a computer to perform a line management method. The method includes receiving prescription information from a hospital information system, selecting an indicator, and associating the selected indicator with the received prescription information. The method further includes creating a label creation request for printing a master label and one or more sub-labels. The master label has at least the received prescription information and the associated indicator, and the one or more sub-labels each include at least the associated indicator.

In yet another aspect, an infusion line management system includes a hospital computer system storing prescription information related to one or more prescriptions associated with a patient. A label generating device receives the prescription information from the hospital computer system, and generates, for each of the one or more prescriptions, a label including a master label and one or more sub-labels related to the corresponding prescription. Each master label includes at least the prescription information and a unique indicator, and each of the sub-labels includes the unique indicator. The one or more sub-labels are individually removable from the master label and affixable to locations throughout the patient infusion system.

DETAILED DESCRIPTION

Figure 1:
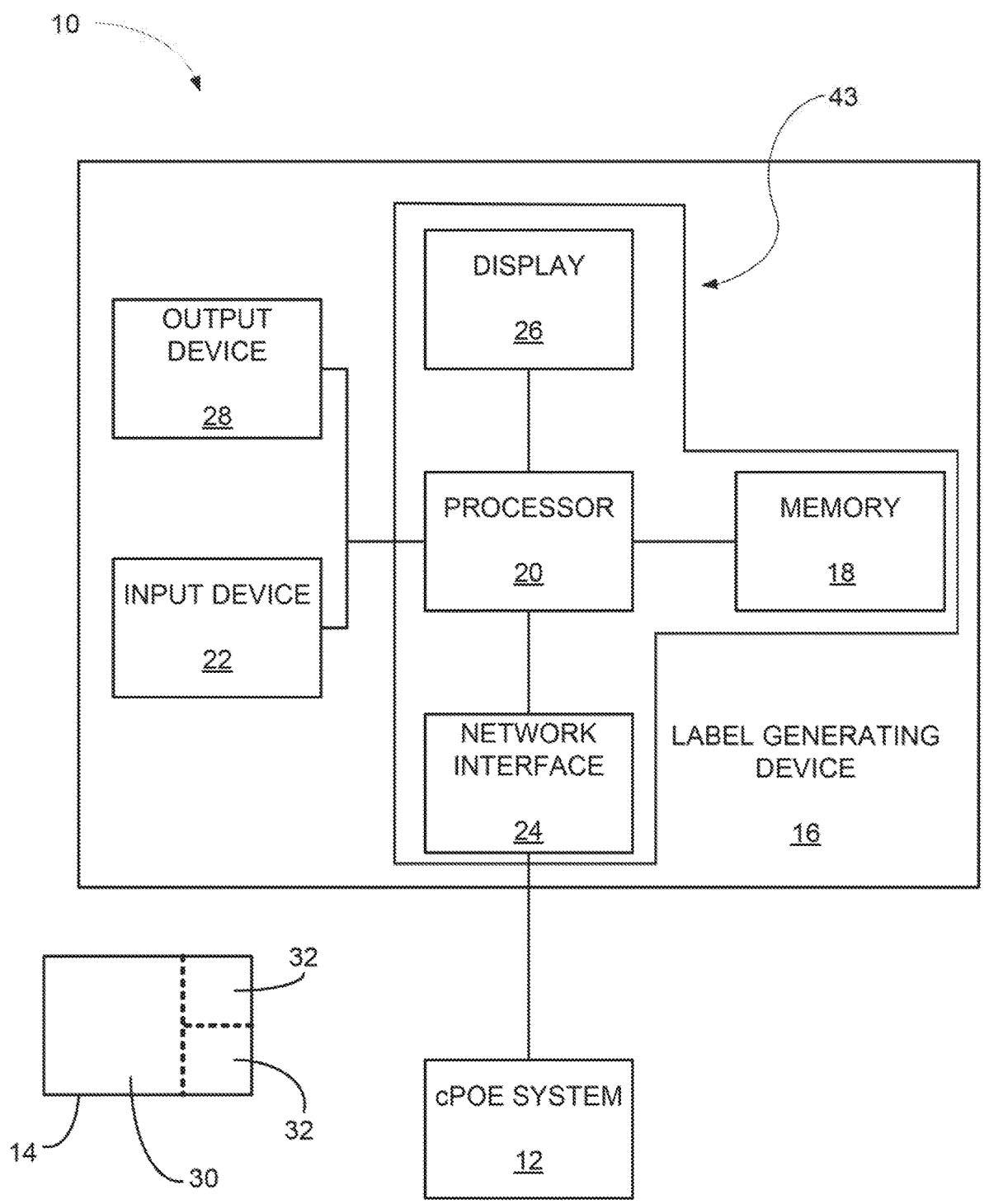
FIG. 1 is a schematic diagram showing the present infusion line management system.

An infusion tube line management system is generally designated 10. As shown in FIG. 1, the system 10 preferably includes a computerized physician/prescriber order entry (cPOE) system 12, a multi-part label 14, and a label generating device 16 used to generate the label. While the description refers to a cPOE system 12, those of skill in the art will recognize that any other computerized system capable of producing required information for printing labels described herein may be used in place of the cPOE system.

The multi-part label 14 is preferably generated as a single entity at the time that a prescription medication is prepared for a patient, and is applied to the medication container (e.g., bag, bottle, syringe, etc.), preferably in a single step. Information transferred to the label 14 is preferably derived from the cPOE system 12.

The cPOE system 12 allows for electronic entry of medical practitioner instructions for the treatment of patients. Typically, hospitals have an existing cPOE system 12 in place, and the line management system 10 preferably interfaces with the existing cPOE system and other hospital information systems such that the line management system receives data from the cPOE system via wired or wireless communications.

The label generating device 16 is preferably located in a hospital or clinic pharmacy for use when prescriptions are filled. As shown in FIG. 1, the label generating device 16 is preferably a computerized device, having at least a memory 18, a processor 20, one or more input devices 22, a network communication interface 24, a display 26, an output device 28, and a power source. The memory 18 is preferably a non-transitory computer-readable recording medium, such as a read only memory (ROM), random access memory (RAM), hard disk, non-volatile flash memory or other electronically erasable programmable read-only memories (EEPROMs), optical or magneto-optical, or other computer-readable storage media. Instructions for operation of the label-generating device 16 are preferably stored on the memory 18.

The device 16 also includes a processor 20, such as a microprocessor or other central processing unit capable of executing instructions stored in the memory 18. The display 26 is a device such as a liquid crystal display, cathode ray tube, plasma display, organic light emitting diode (OLED) display, or any other device capable of outputting data from the memory and processor in a way that is easily discernible by a user. An output device 28, such as a printer, is used to output the multi-part labels 14, preferably at the time a prescription is filled. Alternatively, the labels 14 can be output when the prescription is entered into the cPOE system 12, or when the prescription is delivered to the patient. Additionally, the output device 28 is preferably capable of electronically outputting data to be stored on a nonvolatile memory such as an RFID tag embedded within the label 14.

The network communication interface 24 allows the label-generating device 16 to connect to the cPOE system 12 and/or the hospital information system via a local area network (LAN), wide area network (WAN), and/or the Internet. The network connection interface 24 may be a wired Ethernet connection using, for example, the IEEE 802.3 standard, or a wireless connection using standards such as IEEE 802.11 a/b/g/n/ac, or any newly developed standards that supersede these. The network connection interface 24 may also be used to connect to a cellular data network such as LTE, WiMAX, UMTS, CDMA, HSPA, HSPA+, GPRS, and the like. Still further, the network connection interface 24 may include a Wireless Personal Area Network interface such as a Bluetooth, wireless USB, or other connection as defined in the IEEE 802.15 standards.

Figure 2A:
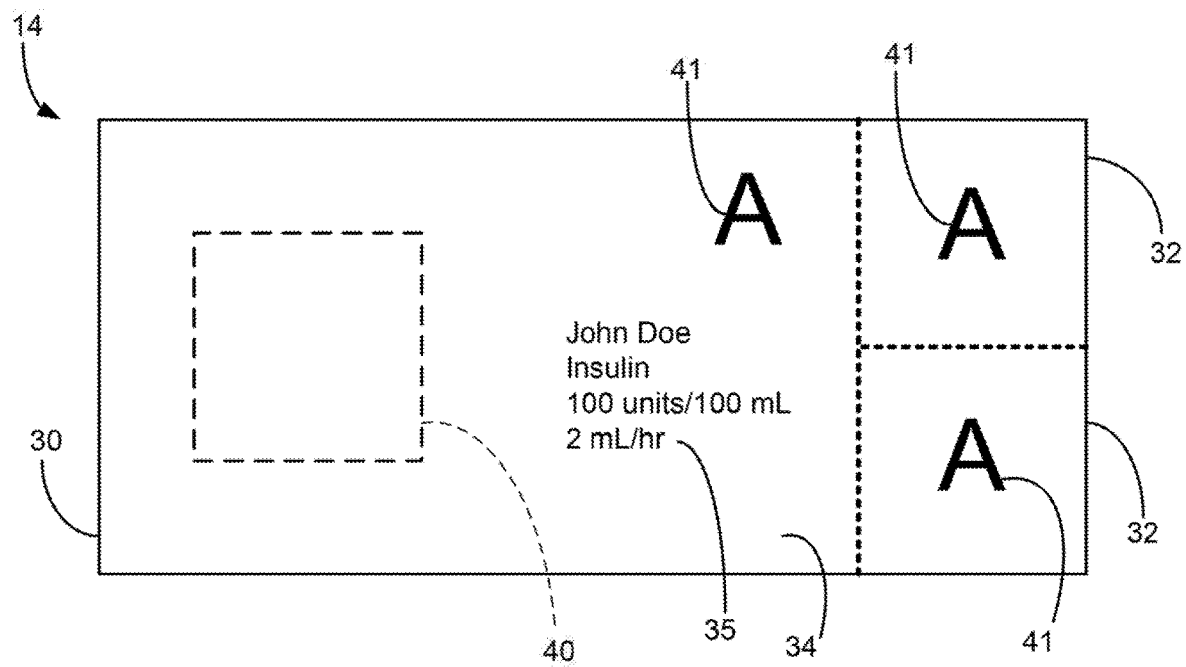
FIG. 2A shows a top plan view of a multi-part label of the infusion line management system of FIG. 1.
Figure 2B:
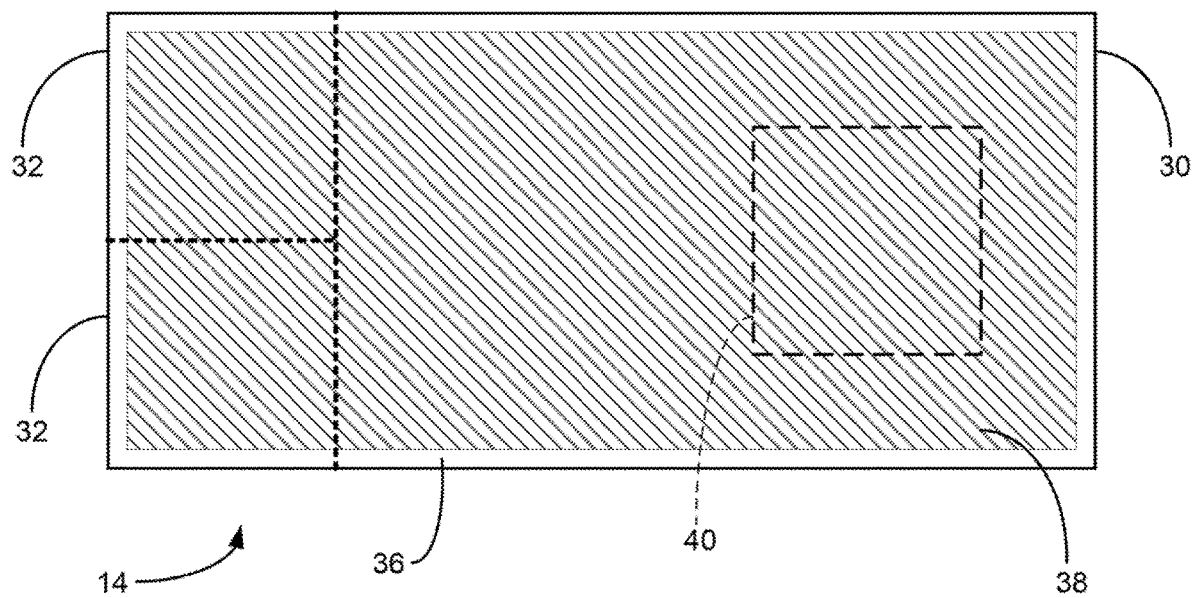
FIG. 2B shows a bottom plan view of a multi-part label of the infusion line management system of FIG. 1.

Each multi-part label 14 preferably includes a master label 30 containing information suitable for the medication container and one or more associated sub-labels 32 removably attached to the master label. Turning now to FIGS. 2A and 2B, at least the master label 30 preferably includes a front surface 34 for displaying prescription information 35 related to the medication, as received from the cPOE system 12, and a rear surface 36 coated in an adhesive 38 such as a pressure-sensitive adhesive.

The information 35 contained on the front surface 34 of the master label 30 may include prescription information represented as human-readable information indicating, for example: medication name, prescribed dosage, patient identifying information, and the like, as well as machine-readable information, such as optically readable data including one or more of a barcode, a QR code, and the like. Alternatively, the master label 30 optionally includes a storage device 40 (shown hidden), such as a radio frequency identification (RFID) tag for electronically storing and transmitting machine readable information. The RFID tag can be affixed to the front surface 34 of the label 14, or embedded within the label.

Additionally, the information 35 contained on the front surface of the master label 30 includes an indicator 41 having a minimal number of human-readable characters (for example, a single alphabet character) used to associate the label and corresponding medication with the infusion system. The indicator 41 preferably also includes other identifying indicia, such as a unique color, pattern, and/or shape. An example of an indicator would therefore be the letter "A", printed in red, on a star-shaped field, and with a cross-hatch pattern. Maintaining the indicator 41 across each of the associated sub-labels reinforces a clinician's ability to quickly and accurately recognize the labels, and thus recognize that certain items in an infusion tubing system are related, tracing a desired line.

Each sub-label 32 preferably includes all or a subset of the information contained on the associated master label. Preferably, each of the sub-labels includes at least the indicator 41 as described above (i.e., unique minimal human-readable characters, color, shape, and/or pattern). Each of the sub-labels 32 is preferably individually separable from the master label 30 and attachable to an element of the infusion system (e.g., the tubing connecting a medication container to a catheter, a pump channel operating on the tubing, etc.). This process of removing sub-labels 32 from the master label 30 on the medication container and attaching them to various elements within the infusion system is performed by the clinician as the medication is first administered to the patient.

Preferably the sub-labels 32 include the indicator 41, without medication-specific information. This advantageously allows the sub-labels 32 and tubing to be re-used even if the medication being delivered is changed. Accordingly, the line management system 10 is preferably optimized to track indicators currently assigned to each medication for a given patient, and reassigns an indicator from a discontinued medication to a replacement medication when it is appropriate to use the same tubing set to administer the replacement medication. The clinician will know that a medication container bearing a reassigned indicator is to be connected to the infusion system at the spike bearing the same indicator. For example, a new medication container bearing the indicator "B" should be connected to the spike that was previously labeled "B." Additionally, the clinician will be able to easily reference which medication is associated with a particular indicator at any point in time by reading the master label, which contains both the medication name and its associated indicator. Thus, the number of times that a clinician is required to re-label a given tubing set is reduced.

Of course, an associated pump channel flow rate may require adjustment when a medication is replaced. This may be set manually by referring to a flow rate printed on the master label on the medication container, or automatically by using a scanner (e.g., RFID reader, barcode scanner, etc.)

to read the machine-readable portion of the master label 30 of the replacement medication if using a pump with this automatic programming capability.

Figure 3A:
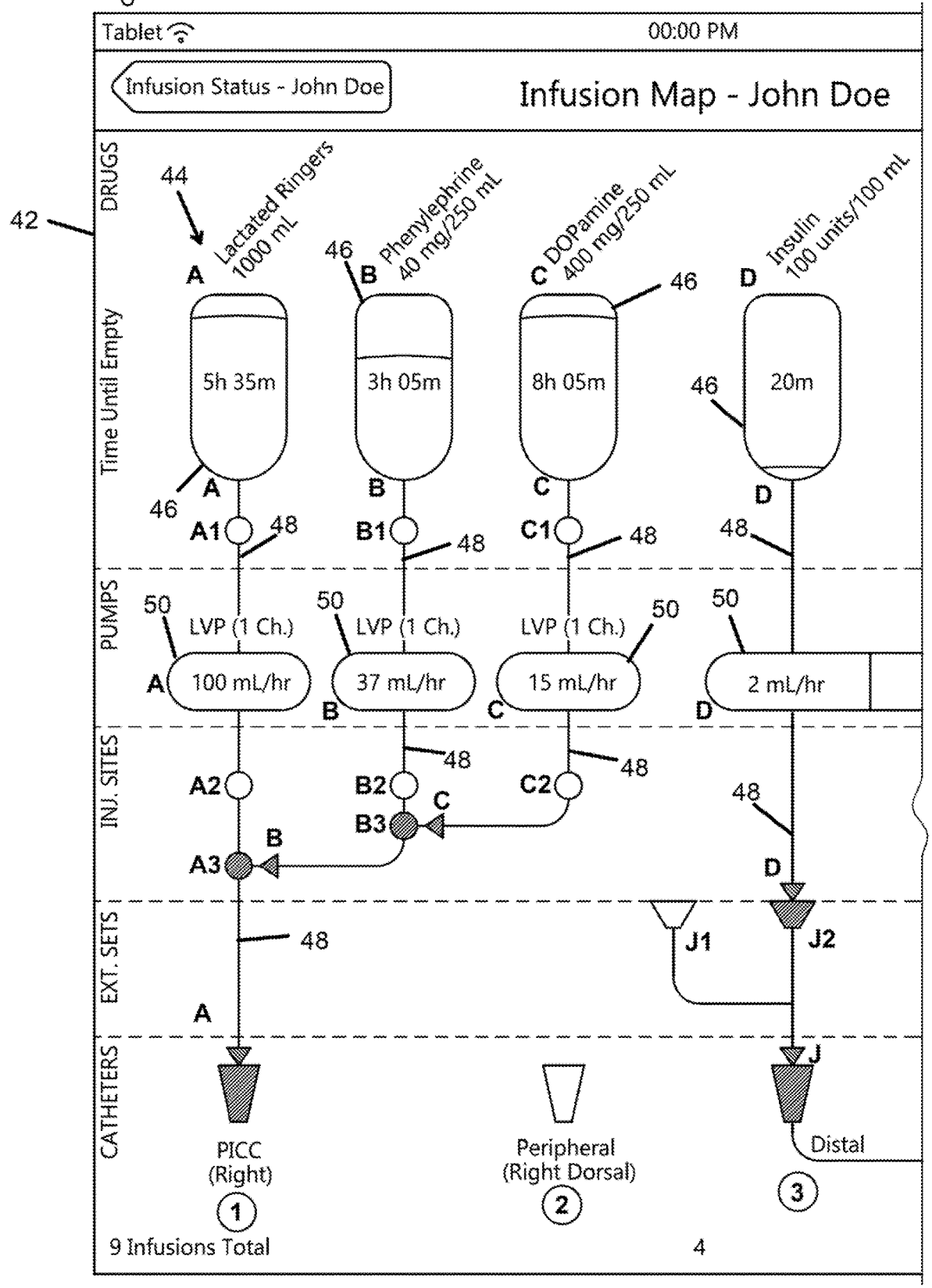
FIGS. 3A and 3B show an example screenshot of a virtual infusion map using the infusion line management system of FIG. 1.
Figure 3B:
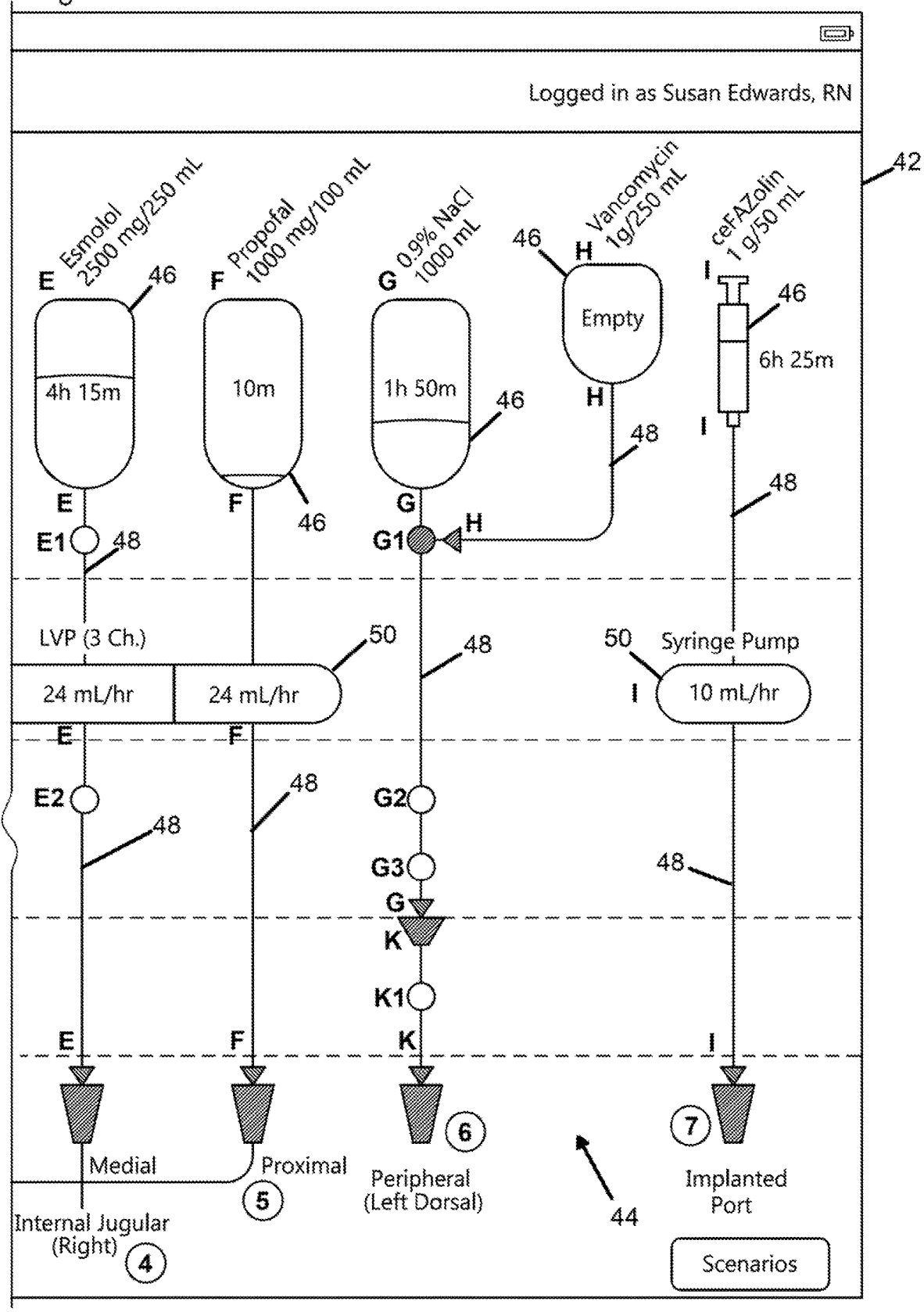

Referring now to FIGS. 3A and 3B, the present infusion line management system 10 is preferably used in conjunction with a patient information software system 43 (see FIG. 1) including a display in the form of an infusion map 42, as shown in FIGS. 3A and 3B. When used in this way, the line management system 10 allows for easy correspondence between the "virtual" infusion map 42 of the patient information software system 43 and the actual infusion system at the patient's bedside. This in turn allows a clinician to look at the infusion map 42 displayed by the patient information software system 43 and quickly locate the corresponding physical item, such as an access port, in the actual infusion tubing system. Moreover, the use of the patient information software system 43 in conjunction with the line management system 10 helps to ensure that the entire infusion system is configured in a safe and effective manner.

As shown in the infusion map display 42, an infusion system 44 includes at least one or more medication containers 46, one or more tubing sets 48 associated with each of the medication containers, and an optional infusion pump 50 configured for administering the medication contained in the one or more medication containers as is well known in the art.

Tubing sets 48 used in infusion tubing systems include a number of access ports, typically between zero and three. Preferably, the tubing set manufacturer will include a prominent number near each access port, starting with the number "1" for the first access port at the spike end of the set, then "2" at the next access port, then "3" and so on. When combined with the clinician-applied sub-labels 32, each access port in the entire infusion setup can be uniquely identified (for example A1, A2, A3, B1, C1, C2, etc. as shown in FIGS. 3A, 3B). This allows the system 10 to unambiguously specify both the tubing set 48 and the particular access port to which a medication should be connected.

Preferably, the multi-part labels 14 are printed at the pharmacy and attached to the medication container before delivery to the patient's bedside. Alternatively, the multi-part labels 14 could be generated on demand at the point of care. The label generating device 16 may take many forms, including a laptop or desktop computer, a client computer integrated with a hospital information system to allow for access at multiple locations (e.g. pharmacy, nursing station, emergency department, diagnostic laboratory, and physician offices), or a portable device such as a laptop computer, tablet, smartphone, personal digital assistant, computer on wheels, workstation on wheels, or a hand-held label maker. Additionally, the computerized device may be integrated into bedside equipment such as smart infusion pumps and/or patient monitors. These alternative devices preferably also communicate with the cPOE via wired or wireless communications methods as discussed above. Alternatively, the label-generating device can be programmed by reading information from the master label on the medication container. Alternatively, the label-generating device could be manually programmed by the clinician at the time of use.

As an alternative to generating physical labels, the system could "write" directly onto the various elements of interest, such as medication containers, tubing sets, etc. For example, the element could receive and retain ink or dye to produce human-readable information on the element. Other methods of information transfer such as electrical, magnetic, thermal, optical, etc. are also contemplated. Examples of such an information transfer method include an erasable programmable read-only memory (EPROM) technology, a radio frequency identification tag, or other non-volatile computer-readable storage device.

While a particular embodiment of the present infusion line management system has been described herein, it will be appreciated by those skilled in the art that changes and modifications may be made thereto without departing from the invention in its broader aspects and as set forth in the following claims.

The invention claimed is:

1. An infusion line management system, including patient infusion system, comprising:
    at least one medication container containing a prescribed medication, and one or more tubing sections forming a tubing set associated with each said at least one medication container;
    a label generating device including a processor, a non-transitory memory, and a display and a printer, which are both connected to said processor, said device configured for receiving prescription information for one or more patient prescriptions;
    at least one printed label, each label having a master label and one or more sub-labels, generated by said label generating device using the received information for each of the prescriptions, each said master label and one or more sub-labels relating to the corresponding prescription, said master label is affixable to said at least one medication container;
    each said master label includes at least human readable information related to the corresponding prescription and additionally includes an indicator identifying a particular portion of the patient infusion system to which said medication container containing the prescription should be connected, said indicator includes a human readable character, as well as an identifying indicia being at least one of a unique color, pattern and shape;
    each of said one or more sub-labels including said indicator without information related to said corresponding prescription, such that said master label and said sub-labels each share said indicator, said one or more sub-labels being individually removable from said master label, and said one or more sub-labels being constructed and arranged to be individually affixable to selected locations throughout the patient infusion system, including at least the one or more tubing sections forming said tubing set, so that all of the selected locations and tubing sections forming said tubing set are provided with said common indicator, for user identification of the portion of the patient infusion system associated with a particular prescribed medication; and
    said processor, said non-transitory memory, and said display being components of a patient infusion software component of a hospital information system, said display receiving information from said hospital information system and generating on said display an infusion map corresponding to an arrangement of the patient infusion system, said map including images of said at least one medication container containing said prescribed medication, and said one or more tubing sections forming said tubing set associated with each said at least one medication container, corresponding locations for each of said master and said one or more sub-labels, said infusion map further including an image of the indicator displayed on the display with at least one of the images of said at least one medication container and an image of the indicator displayed on the display with at least one of the images of said one or more tubing sections, and identifying, using said indicator, the corresponding physical components of the patient infusion system associated with a particular prescribed medication so that the user employs said display in achieving a correspondence between said display and the placement of said master label and said one more sub-labels in said patient infusion system.

2. The infusion line management system of claim 1, wherein said one or more sub-labels includes a plurality of sub-labels affixable to each of said one or more tubing sections.

3. The infusion line management system of claim 1, said label generating device including:
 a network communication interface configured for receiving the prescription information;
 said printer configured for printing the prescription information and the indicator on said master label and the indicator on each of said one or more sub-labels; and
 said processor configured for controlling said network communication interface and said printer.

4. The infusion line management system of claim 3, wherein said printer is capable of writing information to a radio frequency identification tag embedded in said master label, and
 wherein the information includes machine-readable information stored in said radio frequency identification tag.

5. The infusion line management system of claim 1, wherein the information includes both human-readable information and machine-readable information.

6. The infusion line management system of claim 5, wherein the machine-readable information is information represented as an optically readable element.

7. The infusion line management system of claim 1, wherein said master label includes a front surface for displaying the information and said indicator provided by said device, and a rear surface coated in an adhesive and configured for adhesion to medication container, and wherein each of said one or more sub-labels includes a front surface for displaying at least said indicator and a rear surface coated in an adhesive configured for adhesion to said patient infusion system.

8. The infusion line management system of claim 1, wherein said infusion map indicates medications being administered to each patient.

9. The infusion line management system of claim 1, wherein said label generating device is in electrical communication with a cPOE, said label generating device receiving the prescription information from said cPOE.

10. An infusion line management system for assisting a clinician in verifying that each medication is routed through tubing to a correct catheter and that the tube is associated with the correct pump channel, said system comprising:
 a patient infusion system including at least one medication container containing a prescribed medication, one or more tubing sections forming a tubing set associated with each medication container, and at least one infusion pump channel;
 a cPOE storing prescription information related to one or more prescriptions associated with a patient;
 a label generating device including a network communication interface configured for receiving said prescription information, a printer configured for printing said prescription information, and a processor configured for controlling said network communication interface and said printer;
 said label generating device constructed and arranged for receiving said prescription information from said cPOE;
 a label including a master label and one or more sub-labels related to the corresponding prescription generated by said label generating device and corresponding to each of said one or more prescriptions, wherein said master label includes a storage device embedded therein, and wherein the electrical machine-readable data is stored on said storage device;
 each said master label includes a front surface having at least said prescription information and additionally includes a unique indicator identifying a particular portion of said patient infusion system to which said medication container containing said prescription should be connected, and a rear surface having an adhesive for securing said master label to a designated medication container;
 each of said one or more sub-labels including said indicator without said prescription information, such that said master label and said sub-labels each share said indicator, said one or more sub-labels being individually removable from said master label and including a rear surface with an adhesive for securing each of said one or more sub-labels individually to selected locations throughout said patient infusion system, including said one or more tubing sections forming said tubing set and said at least one pump channel, so that all of the selected locations are provided with said common indicator, for user identification of the portion of said patient infusion system associated with a particular prescribed medication;
 said processor being a component of a patient infusion software component of a hospital information system including a display providing an infusion map corresponding to an arrangement of said patient infusion system, said map including images of said at least one medication container containing said prescribed medication, and images of said one or more tubing sections forming said tubing set associated with each said at least one medication container and corresponding locations for each of said master and said one or more sub-labels, said infusion map further including an image of the indicator displayed on the display with at least one of the images of said at least one medication container and an image of the indicator displayed on the display with at least one of the images of said one or more tubing sections, and identifying, using said indicator, the corresponding physical components of said patient infusion system associated with a particular prescribed medication so that the user employs said display in achieving a correspondence between said display and the placement of said master label and said one more sub-labels in said patient infusion system; and
 said indicator being in such a format to allow for exchange of said prescription for at least one new prescription without requiring changing said at least one sub-labels, and said infusion line management system adjusting a flow rate of said at least one infusion pump channel.

11. The infusion line management system of claim 10, wherein the prescription information includes both human-readable information and machine-readable information.

12. The infusion line management system of claim 11, wherein the machine-readable information includes optical machine-readable data.

13. An infusion line management system, including a patient infusion system, comprising:
- at least one medication container containing a prescribed medication;
- one or more tubing sections forming a tubing set associated with each said medication container;
- a label generating device including a processor, a non-transitory memory, and a display and a printer, which are both connected to said processor, said device configured for receiving prescription information for one or more patient prescriptions;
- a printed, human readable label including a master label and one or more sub-labels generated by said label generating device and related to each of said one or more prescriptions, said master label is affixable to one of said medication containers;
- each said master label including at least human readable information related to said corresponding prescription and additionally including an indicator identifying a particular portion of the patient infusion system to which said one of said medication containers should be connected, wherein said master label includes a storage device embedded therein, and wherein electrical machine-readable data is stored on said storage device;
- each of said one or more sub-labels including said indicator without information related to said corresponding prescription, said one or more sub-labels being individually removable from said master label, and said one or more sub-labels being constructed and arranged to be individually affixable to locations throughout the patient infusion system, including at least said one or more tubing section forming said tubing set, so that said one or more tubing sections forming said tubing set are associated with said corresponding prescription contained in said one of said medication containers;
- said processor, said non-transitory memory, and said display being components of a patient infusion software component of a hospital information system, said display receiving information from said hospital information system and generating on said display an infusion map corresponding to an arrangement of the patient infusion system, said map including images of said at least one medication container containing said prescribed medication, at least one infusion pump and said one or more tubing sections forming said tubing set associated with each said at least one medication container and corresponding locations for each of said master and said one or more sub-labels, said infusion map further including an image of the indicator displayed on the display with at least one of the images of said at least one medication container and an image of the indicator displayed on the display with at least one of the images of said one or more tubing sections, and identifying, using said indicator, the corresponding physical components of the patient infusion system associated with a particular prescribed medication so that the user employs said display in achieving a correspondence between said display and the placement of said master label and said one more sub-labels in said patient infusion system; and
- said indicator being in such a format to allow for exchange of said prescription for at least one new prescription without requiring changing said one or more sub-labels, and said infusion line management system adjusting a flow rate of said at least one infusion pump channel.

14. An infusion line management system, said management system comprising:
- a patient infusion system including at least one medication container containing a prescribed medication, one or more tubing sections forming a tubing set associated with each said medication container, and at least one catheter connected to said at least one tubing set, said at least one catheter accessing a patient;
- a patient information software component of a hospital information system including a processor, a non-transitory memory, a display and a network interface;
- an input device connected to said processor, said input device configured to receive prescription information for at least one prescribed medication;
- an output device connected to said processor;
- a printed human readable label, including a master label and one or more sub-labels generated by said output device, for each of said at least one prescribed medication and its associated tubing set, using said received prescription information;
- each said master label being affixed to one of said medication containers, said master label including at least human readable information related to said received prescription information and further including an indicator identifying a particular portion of said patient infusion system to which said medication container should be connected, said master label further including a storage device embedded therein, and wherein electrical machine-readable data is stored on said storage device;
- each of said one or more sub-labels including said indicator without information related to said received prescription information and being affixed to selected locations throughout said particular portion of said patient infusion system, including at least one or more tubing sections, at least one infusion pump and said at least one catheter, so as to facilitate user identification of said particular portion of said patient infusion system to which said medication container should be connected; and
- said display receiving information from said hospital information system and generating on said display an infusion map corresponding to an arrangement of the patient infusion system, said map including images of said at least one medication container containing said prescribed medication, said at least one infusion pump and said one or more tubing sections forming said tubing set associated with each said at least one medication container and corresponding locations for each of said master and said one or more sub-labels, said infusion map further including an image of the indicator displayed on the display with at least one of the images of said at least one medication container and an image of the indicator displayed on the display with at least one of the images of said one or more tubing sections, and identifying, using said indicator, corresponding physical components of said patient infusion system to which said medication container should be connected so as that the user employs said display in achieving a correspondence between said display and placement of said master label and said one more sub-labels in said patient infusion system for maintaining a designated flow rate of said at least one infusion pump depending on the medication in said medication container.

16. The infusion line management system of claim 14, wherein said patient infusion system further includes one or more access ports on said at least one tubing set.

16. The infusion line management system of claim 15, wherein said selected locations further includes said one or more access ports on said at least one tubing set.

* * * * *